(12) United States Patent
Orrock (10) Patent No.: US 8,896,620 B2
(45) Date of Patent: Nov. 25, 2014

(54) COMPUTER INPUT DEVICE

(75) Inventor: Jared M. Orrock, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 690 days.

(21) Appl. No.: 13/254,401

(22) PCT Filed: Mar. 4, 2010

(86) PCT No.: PCT/US2010/026217
§ 371 (c)(1),
(2), (4) Date: Nov. 14, 2011

(87) PCT Pub. No.: WO2010/102113
PCT Pub. Date: Sep. 10, 2010

(65) Prior Publication Data
US 2012/0092247 A1    Apr. 19, 2012

Related U.S. Application Data

(60) Provisional application No. 61/157,425, filed on Mar. 4, 2009.

(51) Int. Cl.
| | | |
|---|---|---|
| G09G 5/08 | (2006.01) | |
| G09G 5/00 | (2006.01) | |
| G09G 5/02 | (2006.01) | |
| G06F 3/048 | (2013.01) | |
| G06F 19/00 | (2011.01) | |

(52) U.S. Cl.
CPC .................................. *G06F 19/321* (2013.01)
USPC ........... 345/589; 345/581; 345/619; 345/649; 345/214; 345/161; 715/831; 715/856

(58) Field of Classification Search
USPC ......... 345/581, 589, 619, 649, 653, 654, 660, 345/670, 204, 214, 156–161, 164, 166, 345/168; 715/831, 833, 856, 857
See application file for complete search history.

(56) References Cited

U.S. PATENT DOCUMENTS

| | | | |
|---|---|---|---|
| 5,923,318 A | 7/1999 | Zhai et al. | |
| 5,963,197 A | 10/1999 | Bacon et al. | |
| 6,031,518 A | 2/2000 | Adams et al. | |
| 2004/0150621 A1* | 8/2004 | Bohn | ............................ 345/163 |
| 2008/0174550 A1 | 7/2008 | Laurila et al. | |

(Continued)

FOREIGN PATENT DOCUMENTS

| | | |
|---|---|---|
| EP | 1429236 A1 | 6/2004 |
| WO | WO 96-31836 A1 | 10/1996 |

OTHER PUBLICATIONS

Abramowitz and Davidson, "Microscope Stages" [online]. The Florida State University, Tallahassee, Florida, copyright 1998-2012, last modified on Aug. 3, 2003 [retrieved on Dec. 12, 2008]. Retrieved from the Internet: http://www.microscopy.fsu.edu/primer/anatomy/stage.html; 7 pgs.

(Continued)

*Primary Examiner* — Wesner Sajous
(74) *Attorney, Agent, or Firm* — Mueting, Raasch & Gebhardt, P.A.

(57) ABSTRACT

Computer input devices are described herein for use in manipulating digital images on a display apparatus.

21 Claims, 4 Drawing Sheets

(56) References Cited

U.S. PATENT DOCUMENTS

| | | | |
|---|---|---|---|
| 2009/0201248 A1* | 8/2009 | Negulescu et al. | 345/157 |
| 2010/0251180 A1* | 9/2010 | Cragun et al. | 715/834 |
| 2011/0032187 A1* | 2/2011 | Kramer et al. | 345/163 |
| 2012/0068928 A1* | 3/2012 | Bruss et al. | 345/163 |

OTHER PUBLICATIONS

Giszczynski, "Telepathology: Revolution or Evolution?" *Medical Laboratory Observer*, Sep. 1, 2007; 39(9): 38.

*Galileo Computer Based Microscope* [online]. Joe's Sports, copyright 2001 [retrieved on Dec. 10, 2008]. Retrieved from the Internet: http://www.joesports.com/product/index.jsp/productId=2296937; 2 pgs. Webpage no longer available.

*Mouse* (*computing*) [online] Wikipedia, date unknown [retrieved on Dec. 10, 2008]. Retrieved from the Internet: http://en.wikipedia.org/wiki/Computer_mouse; 18 pgs.

*Prime Entertainment QX-5* [online]. Amazon.com copyright 1996-2008 [retrieved on Dec. 10, 2008]. Retrieved from the Internet: http://www.amazon.com/Prime-Entertainment-QX5-ENTERTAINMENT-Microscope/dp...; 7 pgs.

*QX5 Computer Microscope* [online]. 110220VOLTS.com, Glendale Heights, IL, copyright 2002-2008 [retrieved on Dec. 10, 2008]. Retrieved from the Internet: http://www.110220volts.com/DB12011.html; 1 pg.

International Preliminary Report on Patentability, issued Sep. 6, 2011 for International Patent Application No. PCT/US2010/026217, filed Mar. 4, 2010, 5 pgs.

International Search Report, mailed Sep. 28, 2010 for International Patent Application No. PCT/US2010/026217, filed Mar. 4, 2010, 2 pgs.

Written Opinion of the International Searching Authority, mailed Sep. 28, 2010 for International Patent Application No. PCT/US2010/026217, filed Mar. 4, 2010, 4 pgs.

* cited by examiner

COMPUTER INPUT DEVICE

RELATED APPLICATION

The present application is a U.S. National Stage Application of International Application No. PCT/US2010/026217, titled COMPUTER INPUT DEVICE, filed on Mar. 4, 2010, published in the English language on Sep. 10, 2010 as International Publication No. WO 2010/102113 A2, which claims the benefit under 35 U.S.C. §119(e) of U.S. Provisional Application Ser. No. 61/157,425, titled COMPUTER INPUT DEVICE, filed on Mar. 4, 2009, both of which are incorporated herein by reference in their entirety.

The present disclosure relates to a computer input device (e.g., a virtual microscope driver) for use in, for example, manipulating medical diagnostic and other digital images.

Despite recent improvements in digital pathology technology, some improvements in technology have been incorporated into routine clinical use on a limited basis. In the field of radiology, digital imaging or digital imaging and communications in medicine (DICOM) has become the standard of practice. Current radiology residents may never practice in a setting that will require the use of a light box, a once-crucial piece of equipment used to view radiographic films. Radiology was quick to adopt DICOM technology in part because radiographic films are standardized, the instrumentation can be adjusted by a technician until quality images are obtained, and also because it was quickly realized that the quality of care did not diminish if the radiologist signed out cases via computer.

On the other hand, the process of rendering a diagnosis on a digital image of a tissue specimen may be far more difficult than making diagnoses on digitized radiographic images for several reasons, most of which have and have had to do with the technical limitations of current technology (e.g., computing technology).

Digital pathology may presently include digitizing images from slides which can then be stored, transmitted, viewed, and manipulated using a computer, much like may be done in radiology. Scanners and software packages may allow the pathologist to see the digital images at various magnifications and may have an image stacking function, which is a process that allows for multiple levels (e.g., scanned in at different focal lengths) of a slide to be stacked together, so that a computer may recapitulate the up and down focus through a section of tissue as would be visualized with a traditional microscope. This may be useful because, while the microscopic tissue section on a slide may seem two-dimensional, the microscopic tissue section does have a depth and therefore focusing up and down on a slide may be a useful way that pathologists may obtain information from a slide (e.g., to identify bacteria or to look at nuclear detail).

One problem with implementing this technology has been inadequate computing memory and/or processing speed to process these very large images in real time.

Another problem with implementing digital pathology imaging into routine clinical practice may be the awkwardness of using existing modalities to control and manipulate the digital images. Presently, digital slide images may be viewed on a computer screen (e.g., a large high-resolution screen) and are manipulated with a mouse and computer keyboard interface. Such an interface may be not only slow and cumbersome as compared to the traditional slide and microscope, but also may be an unfamiliar way for a pathologist to look at histological images. For example, with a traditional microscope, a pathologist may scan (e.g., view) a slide at low magnification and find a region of interest within seconds while simultaneously adjusting the focus as needed. Once the region of interest is identified, the magnification may instantly be changed as needed to make a diagnosis. By being able to simultaneously change the focus and magnification of an image, in combination with the ability to move to any region of the slide extremely rapidly by physically moving the slide across a microscope stage, a pathologist may very efficiently see the relevant material and make an accurate diagnosis. When this process is attempted using a conventional mouse and keyboard, the process may take orders of magnitude longer, even though the images may be of sufficient diagnostic quality.

SUMMARY

Computer input devices are described herein for use in manipulating digital images on a display apparatus in, for example, medical diagnostics. A computer input device as described herein may be particularly useful for manipulation of one or more digital images such as, for example, digital histological images, including but not limited to images of a microscopic tissue section.

Manipulation of digital histological images using a mouse and computer keyboard interface may be challenging due to, for example, the location of controls that may not be familiar or intuitive to a pathologist. Further, simultaneous manipulation of, for example, focus and magnification of very large images may not be possible with traditional computer interface devices (e.g., mouse, computer keyboard, etc.).

A device in accordance with the present disclosure may, for example, increase efficiency in making diagnoses on digital histological images by decreasing time per diagnosis, and increasing ease of implementation by pathologists. In some embodiments, the computer input device may generally resemble a traditional light microscope and may include controls that are analogous to controls used in traditional light microscopy. In some embodiments, the computer input device may include additional controls that may provide additional functionality. In some embodiments, the computer input device may have one or more duplicate controls, such that the device may be operated in a similar manner by either left-handed users and/or right-handed users.

With greater ease of use and/or increased efficiency of use, a computer input device of the present disclosure may potentially lead to greater productivity in making diagnoses from microscopic tissue sections. Computer input devices of the present disclosure may reduce the cost of making a diagnosis and may also eliminate costs of acquiring, sterilizing, and maintaining traditional microscopic equipment as well as office space and personnel required to perform such tasks. For example, a pathologist located remotely from the referring physician and/or patient could receive the histological images and other data, provide diagnoses or other evaluations, and obtain the professional fee for this service without requiring that the pathologist be physically present at the facility where the histological slides are made.

In one aspect, embodiments of a computer input device as described herein for manipulating a digital image displayed on a display apparatus operably connected to the computer input device may include: a housing having a base with a bottom portion for optionally resting on a support surface, an arm extending upward from the base and terminating at a top portion, and a stage extending outward from the arm at a location intermediate the base and the top portion. The stage comprises a distal portion proximate the arm, a proximal portion opposite the distal portion, wherein a y-axis passes through the distal portion, the proximal portion, and the arm, wherein the stage further comprises a top surface defining an xy-plane, wherein the xy-plane optionally generally aligns with the bottom portion of the base, wherein the xy-plane comprises the y-axis and an x-axis transverse to the y-axis. An x-axis stage controller is attached to the housing and configured to communicate lateral movement of the digital image displayed on the display apparatus along an x-axis, the x-axis stage controller optionally extending from the stage and optionally rotatable about a first axis that may be generally aligned with the z-axis, wherein the z-axis is generally transverse to the xy-plane. A y-axis stage controller is attached to the housing and configured to communicate lateral movement of the digital image displayed on the display apparatus along a y-axis, the y-axis stage controller optionally extending from the stage and optionally rotatable about a second axis that may be generally aligned with the z-axis, wherein the first and second axes are, optionally, the same axis.

In some embodiments, the computer input device further comprises a brightness controller configured to change brightness of the digital image displayed on the display apparatus; wherein the brightness controller optionally extends from the base toward the stage and optionally rotates about a third axis optionally generally aligned with the z-axis.

In some embodiments, the computer input device further comprises a coarse focus controller configured to change focus of the digital image displayed on the display apparatus, wherein the coarse focus controller optionally extends from the arm and optionally rotates about a fourth axis optionally generally aligned with the x-axis. In some embodiments, the computer input device further comprises a fine focus controller configured to change focus of the digital image displayed on the display apparatus, wherein the fine focus controller optionally extends from the arm and optionally rotates about a fifth axis optionally generally aligned with the x-axis, wherein the fourth and fifth axes are optionally the same axis.

In some embodiments, the computer input device further comprises an objective change controller configured to change magnification of the digital image displayed on the display apparatus, wherein the objective change controller optionally extends from the base toward the stage and optionally rotates about a sixth axis optionally generally aligned with the z-axis. In some embodiments, the objective change controller is configured to select one of a plurality of discrete magnifications when changing the magnification of the digital image displayed on the display apparatus.

In some embodiments, the computer input device further comprises an objective selector element attached to the housing and configured to change magnification of the digital image displayed on the display apparatus.

In some embodiments, the computer input device further comprises an image selector element attached to the housing and configured to create a new digital image including all or a portion of the digital image displayed on the display apparatus.

In some embodiments, the computer input device further comprises an advancement selector element attached to the housing and configured to selected a different digital image for display on the display apparatus. In some embodiments, the advancement selector element comprises a next selector element for selecting digital images pre-loaded in a digital queue.

In some embodiments, the computer input device further comprises a stain selector element attached to the housing and configured to toggle between stained portions of the digital image displayed on the display apparatus.

In some embodiments, the computer input device further comprises a stain adjustment controller attached to the housing and configured to adjust the stained appearance of all or a portion of the digital image displayed on the display apparatus.

In some embodiments, the computer input device further comprises a display toggle selector element attached to the housing and configured to toggle a display on the display apparatus between a full screen, split screen, and other screen configurations.

In some embodiments, the computer input device further comprises a marking selector element attached to the housing and configured to mark at least a portion of the digital image displayed on the display apparatus.

In some embodiments, the computer input device further comprises a drawing selector element attached to the housing and configured to digitally draw on the digital image displayed on the display apparatus. In some embodiments, the drawing selector element is configured to draw indicia on the digital image.

In some embodiments, the computer input device further comprises a pointer controller attached to the housing and configured to manipulate a pointer or cursor on the digital image displayed on the display apparatus, wherein the pointer controller is optionally a joystick controller or a roller ball controller.

In some embodiments, the computer input device comprises a slide sensor pad on the top surface of the stage, the slide sensor pad comprising one or more sensors configured to detect movement on the slide sensor pad within the xy-plane.

In some embodiments of the computer input device that include a slide sensor pad, the computer input device comprises a reference slide and wherein the one or more sensors are configured to detect movement of the reference slide on the slide sensor pad. In some embodiments, the reference slide comprises a design on one or more sides of the reference slide. In some embodiments, movement of the reference slide on the slide sensor pad translates to movement of the digital image displayed on the display apparatus.

In one or more embodiments, focus controllers may be actuated simultaneously with actuating the objective selector element or the objective change controller.

In one or more embodiments, the computer input device may include a reference slide. Detecting movement within the xy-plane may include detecting movement of the reference slide on the slide sensor pad. The reference slide may be constructed of glass or any other suitable material or combination of materials. The reference slide may include a design on one or more sides of the reference slide. Movement of the reference slide on the slide sensor pad may optionally translate to movement of the digital image on a digital image display apparatus operably connected to the computer input device.

In one or more embodiments, the computer input device controls a digital image on a display apparatus that is operably connected to the computer input device. The digital image may be a scanned digital image of biological material. The digital image may include a virtual stack of digital images.

In one or more embodiments, the slide sensor pad may include an optical sensor.

In one or more embodiments, the computer input device controllers and selector elements each correspond with a feature of image display software.

In one or more embodiments, an advancement selector element may include a next selector element and a previous selector element, each for selecting biological cases pre-loaded in a digital queue (e.g., a series of images in a virtual stack, etc.).

In one or more embodiments, the computer input device has a shape that generally resembles a microscope.

In one or more embodiments, the objective change controller may be actuated to select one of a plurality of discrete magnifications or to select a magnification different than the discrete magnifications.

In one or more embodiments, the distance between the bottom portion of the base of the housing and the coarse focus controller is adjustable.

In one or more embodiments, the distance between the bottom portion of the base of the housing and the fine focus controller is adjustable.

In one or more embodiments, actuating the image selector element creates a new digital image optionally comprising the image displayed on the display apparatus.

In one or more embodiments, the device may include a contrast controller for adjusting contrast of a displayed digital image.

In one or more embodiments, the device may include a stain adjustment controller for correction of over/under-stained scanned images.

In one or more embodiments, actuating the drawing selector element allows digitally drawing on the digital image, wherein digitally drawing on the digital image optionally includes drawing indicia that identifies regions of interest in the digital image, wherein digitally drawing on the digital image optionally includes drawing a perimeter around a region for further analysis based on computer assisted diagnostic (CAD) algorithms.

In one or more embodiments, the pointer controller is for pointing to regions of interest in the digital image or optionally digitally drawing on the digital image.

In one or more embodiments, actuating the marking selector element is for marking at least a portion of the digital image for photographing or future reference.

In one or more embodiments, the display toggle selector element is for toggling the screen display on the display apparatus between full screen, split screen, and other screen configurations, optionally wherein actuating the display toggle selector element is for simultaneously displaying a plurality of immuno stains of the same case and optionally allowing comparison of immuno expression with the cells of interest on H and E.

The words "preferred" and "preferably" refer to embodiments that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein and in the appended claims, the singular forms "a," "an," and "the" include plural references unless explicitly limited to the singular form or the context clearly dictates otherwise.

The term "and/or" means one or all of the listed elements or a combination of any two or more of the listed elements.

The above summary is not intended to describe each embodiment or every implementation of the present disclosure. Rather, a more complete understanding of the disclosure will become apparent and appreciated by reference to the following Description of Illustrative Embodiments and claims in view of the accompanying figures of the drawing.

DESCRIPTION OF ILLUSTRATIVE EMBODIMENTS

In the following description of illustrative embodiments, reference is made to the accompanying figures of the drawing which form a part hereof, and in which are shown, by way of illustration, specific embodiments of computer input devices and methods of using the same. It is to be understood that other embodiments may be utilized and structural changes may be made without departing from the scope of the present invention.

In one aspect, the present disclosure provides a computer input device for manipulating a digital image, wherein the device includes a housing that includes a base, an arm extending upward from the base and a stage 40 extending outward from the arm at a location intermediate the base 20 and the top of the arm.

As used herein, manipulation of a digital image may include, but is not limited to translationally moving a digital image across a screen of a display apparatus, changing focus, changing magnification, inserting markings or annotations, and otherwise changing a digital image or the display thereof on a display apparatus. Manipulation of a digital image may further include, for example, using various computer functions from one or more menus available in a software program or an operating system, such as to open, close, upload, save, etc. a digital image. Manipulation of a digital image may further include adjusting display settings on a display apparatus, such as tint, contrast, brightness, etc.

As used herein, a display apparatus is an apparatus operably connected to the computer input device and capable of displaying one or more digital images for viewing (e.g., on a screen).

Figure 2:
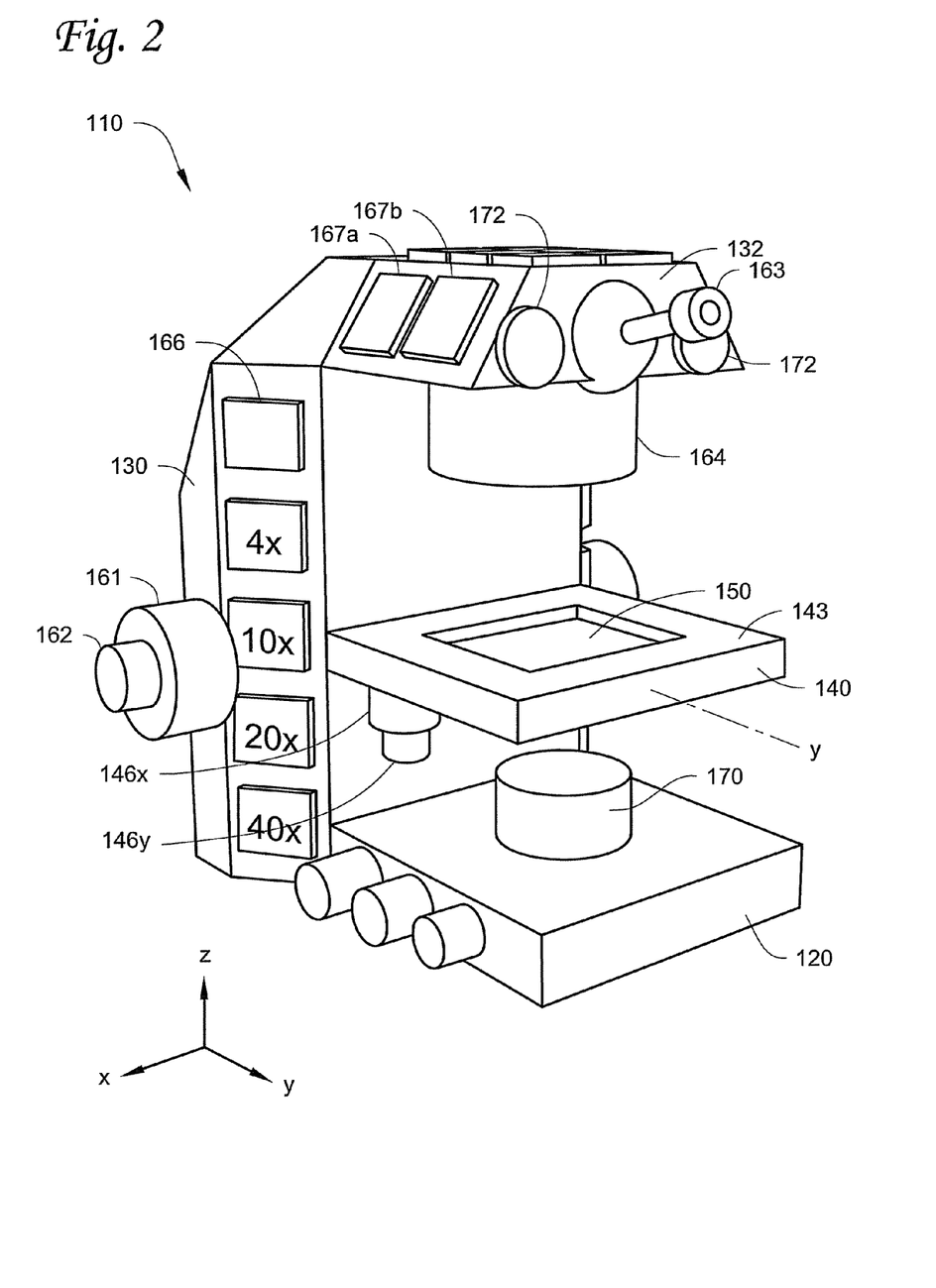
FIGS. 2-4 each depict, from various directions, a perspective view of one exemplary computer input device according to the present disclosure.
Figure 3:
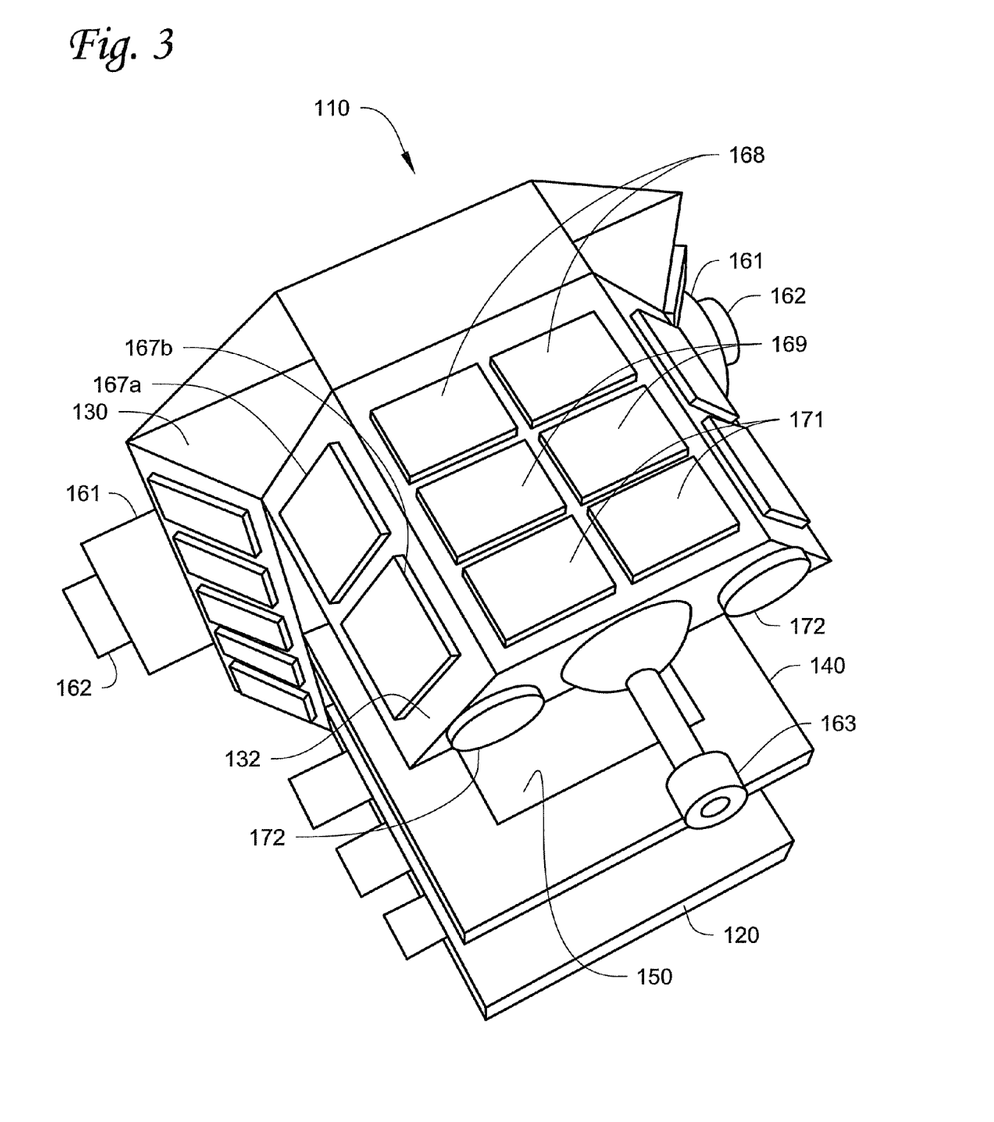
Figure 4:
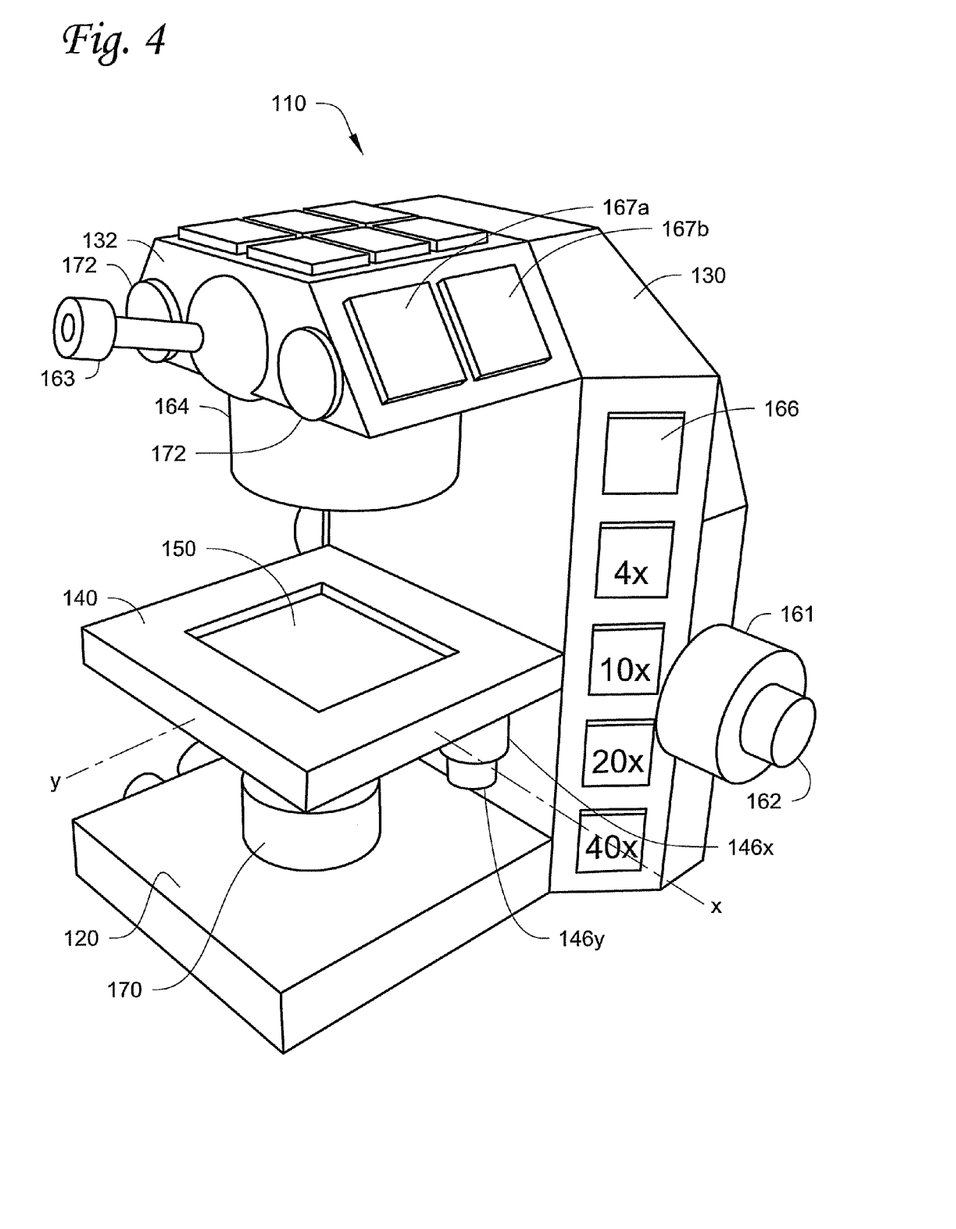

Referring to, e.g., FIGS. 2-4, in some embodiments the base 120 of the housing 110 of the computer input device may have a bottom portion for optionally resting on a support surface. In some embodiments, the bottom portion of the base 120 of the housing 110 may be flat. Preferably, the center of gravity of the computer input device is located above the bottom portion of the base 120 such that the computer input device remains generally upright, wherein the bottom portion of the base 120 rests on the support surface. Alternatively, the base 120 may optionally be removably installed or otherwise removably attached to any type of support surface including, but not limited to a table, a laboratory bench, a computer work station, a wall, or any other suitable surface.

In one or more embodiments, the stage 140, extending outward from the arm 130, may include a distal portion proximate the arm 130 and a proximal portion opposite the distal portion, wherein a y-axis may pass through the distal portion, the proximal portion, and the arm 130. In some embodiments, the y-axis may be horizontal and may also be perpendicular to the arm 130. The stage 140 may also include a top surface that may be optionally horizontal. The top surface of the stage 140 may define an xy-plane, wherein the xy-plane may generally align with the bottom portion of the base, and wherein the xy-plane includes the y-axis and an x-axis. Preferably, the x-axis is transverse to the y-axis.

Figure 1:
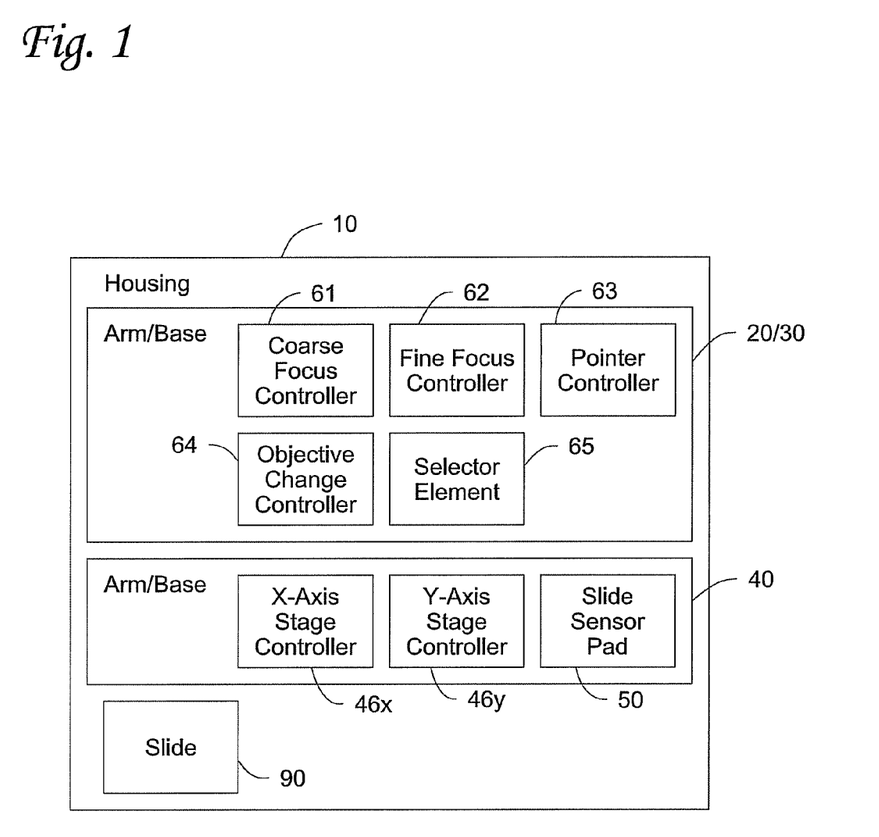
FIG. 1 is a block diagram representing a computer input device of the present disclosure.

In one or more embodiments of the present disclosure, a computer input device may include various controls (e.g., controllers, selector elements, etc.) and/or sensors, which may be located on the computer input device in a wide variety of configurations. FIG. 1 contains a block diagram of at least one embodiment of the present disclosure that may include a computer input device having a housing 10, wherein the housing 10 may include a base/arm 20/30, and a stage 40. A wide variety of arrangements of controllers and selector elements in the computer input device are available according to the present disclosure. For example, in FIG. 1, the computer input device is configured in one particular arrangement, such that either the arm 20 or the base 30 may include an optional coarse focus controller 61, a fine focus controller 62, an optional pointer controller 63, an objective change controller 64, and one or more optional selector elements 65. Further, in FIG. 1, the stage 40 may include a slide sensor pad 50, an optional x-axis stage controller 46*x*, and an optional y-axis stage controller 46*y*. While the optional x-axis and y-axis stage controllers 46*x* and 46*y* are preferably located on or proximal to the stage, as depicted in the configuration in FIG. 1, these may be optionally located on the computer input device in any location. Although not shown in FIG. 1, the computer input device of FIG. 1 may further include other selector elements (e.g., other functional selector elements), controllers, and sensors, including those unrecited and/or duplicates of those recited.

In the present disclosure, the stage may also include a slide sensor pad. Referring to the embodiment depicted in, e.g., FIGS. 2-4, the slide sensor pad 150 is optionally located on the top surface 143 of the stage 140. The slide sensor pad 150 may include one or more suitable sensors capable of detecting movement within the xy-plane (e.g., movement of an object on the slide sensor pad). For example, a slide sensor pad may include a touch pad that is capable of detecting movement of, for example, a fingertip, a stylus tip, or other directing object. A slide sensor pad may be capable of detecting movement of an optional reference slide (e.g., movement of the reference slide across the stage). In some embodiments, the slide sensor pad may include an optical sensor that may be capable of detecting movement of an object (e.g., a reference slide, etc.) proximate the optical sensor. In some embodiments, the computer input device may transmit a signal that allows detection of movement within the xy-plane, which may, in some embodiments, be translated to translational movement of a digital image on a display apparatus (e.g., a large high-resolution computer monitor, a television screen, a projection on a screen, etc.). In one or more embodiments, movement of a reference slide on the slide sensor pad may be translated to movement of a digital image on a display screen. In an embodiment depicted in FIG. 2, the slide sensor pad can be seen on the top surface of the stage. In FIGS. 3 and 4, the slide sensor pad 150 can also be seen on the top surface 143 of the stage 140.

The device may include an x-axis stage controller 46*x*/146*x* and a y-axis stage controller 46*y*/146*y*. For example, the stage 40/140 may include an x-axis stage controller 146*x* and a y-axis stage controller 146*y*. The x-axis and y-axis stage controllers may take any suitable form or shape (e.g., one or more dials, knobs, touch pads, buttons, etc.) for manipulation by a user. In one or more embodiments wherein the computer input device is used to, for example, manipulate the display of a digital image, actuation of the x-axis stage controller may be used to communicate a lateral movement of the digital image on the display apparatus in a prescribed direction (e.g., the x-axis). Likewise, in such embodiments, actuation of the y-axis stage controller may be used to communicate a lateral movement of the digital image on the display apparatus in a different prescribed direction (e.g., the y-axis).

In one or more embodiments, the x-axis stage controller 146*x* may extend from the stage and may be rotatable about a first axis. Likewise, the y-axis stage controller 146*y* may, for example, extend from the stage and may be rotatable about a second axis. The first and/or second axes may be optionally generally aligned with a z-axis. The z-axis may be transverse to the xy-plane. Further, the first and second axes may, in some embodiments, be the same axis. For example, the x-axis and y-axis stage controllers may rotate about the same axis. In one or more preferred embodiments, the x-axis and y-axis stage controllers generally resemble the corresponding stage controls of a traditional light or optical microscope.

In some embodiments, the coordinates of a digital image of a slide may be able to be noted when using the x-axis and y-axis stage controllers, just as coordinates of a slide are noted when using a traditional light microscope. However, since a digital image may have known dimensions, the coordinates may be described even without using the x-axis and y-axis stage controllers (e.g., the coordinates may be determined within, for example, image display software, etc). In an embodiment depicted in FIG. 2, the x-axis and y-axis stage controllers 146*x* and 146*y* can be seen extending from the underside of the stage 140, which extends outwardly from the arm 130.

In FIG. 4, a second set of x-axis and y-axis stage controllers 146*x* and 146*y* can be seen extending from the underside of the stage. A computer input device having duplicate controllers (e.g., x-axis stage controllers, y-axis stage controllers, etc.), one on each side of the device, may allow the device to be similarly used by right-handed or left-handed users. The optional provision of duplicate controllers and/or selector elements in computer input devices is described further herein.

In some embodiments of the present disclosure, actuation of the x-axis and/or y-axis stage controllers 146*x* and 146*y* may optionally cause movement (e.g., translational movement) of some other portion of the stage 140 of the computer input device and/or movement (e.g. translational movement) of an optional reference slide (e.g., slide 90 as described in connection with FIG. 1) on the stage. In some embodiments, actuation of the x-axis and y-axis stage controllers results in no physical movement of the stage or reference slide, but rather may cause the digital image on a display apparatus to move in a selected manner.

In one or more embodiments, the device may further include a brightness controller. The brightness controller may take any suitable form or shape (e.g., one or more dials, knobs, touch pads, buttons, etc.) for manipulation by a user. For example, a brightness controller 170 may extend from the base in a direction toward the stage. The brightness controller may be rotatable about a third axis, which may be generally aligned with the z-axis. In one or more embodiments wherein the computer input device is used to, for example, manipulate the display of a digital image, actuation of the brightness controller may be used to communicate, for example, a change in the brightness of the display apparatus or to change color settings in the display apparatus. In one or more preferred embodiments, the brightness controller may generally resemble the light and/or condenser controls of a traditional light microscope. In an embodiment depicted in FIGS. 2 and 4, the brightness controller 170 can be seen extending from the base.

In one or more embodiments of the present disclosure, the device may optionally include a coarse focus controller 61/161 and/or a fine focus controller 62/162. The coarse and/or fine focus controllers may take any suitable form or shape (e.g., one or more dials, knobs, touch pads, buttons, etc.) for manipulation by a user. For example, the coarse and/or fine focus controllers 161 and 162 may extend from the arm 130 and may be rotatable about a fourth axis and fifth axis, respectively. In some embodiments, the fourth and/or fifth axes may be generally aligned with the x-axis. In some embodiments, the fourth and fifth axes may be the same axis (as, e.g., depicted in FIG. 2).

In one or more embodiments wherein the computer input device is used to, for example, manipulate the display of a digital image, actuation of the coarse and/or fine focus controllers may be used to communicate, for example, a change in the focus of an image on the display apparatus. In one or more preferred embodiments, the coarse and fine focus controllers generally resemble the coarse and fine focus controls of a traditional microscope.

In one or more embodiments, the computer input device may include only one focus controller (e.g., a fine focus controller). For example, a coarse focus controller may not be needed in some situations (e.g., when digital images have been scanned while essentially in focus). In an embodiment depicted in FIG. 2, the coarse and fine focus controllers 161 and 162 can be seen extending from the arm 130. In FIGS. 3 and 4, a second set of coarse and fine focus controllers 161 and 162 can be seen extending from the arm 130 in the opposite direction.

In one or more embodiments, the device may include an objective change controller 64/164. The objective change controller may take any suitable form or shape (e.g., one or more dials, knobs, touch pads, buttons, etc.) for manipulation by a user. For example, the objective change controller may extend from the top portion optionally toward the stage. The objective change controller may be optionally rotatable about a sixth axis. In some embodiments, the sixth axis may be generally aligned with the z-axis. In one or more embodiments wherein the computer input device is used to, for example, manipulate the display of a digital image, actuation of the objective change controller may be used to communicate, for example, a change in the magnification an image on the display apparatus. In one or more preferred embodiments, the objective change controller may generally resemble the objective controls of a traditional light microscope. For example, the objective change controller 164 may resemble a rotatable turret.

In some embodiments, the objective change controller 164 may be designed to allow a user to select one of a plurality of discrete magnifications (e.g., 4×, 10×, 20×, 40×) and/or to select a magnification different than the discrete magnifications (e.g., 4.5×, 5×, 6.75×, 7.03×, 13×, 27×, etc.). For example, in some embodiments, the objective change controller may be manipulated to select any magnification from a range of available magnifications based on, for example, the magnifications used when scanning a microscopic tissue section into a digital image (e.g., a histological digital image). In an embodiment depicted in FIG. 2, the objective change controller 164 can be seen extending from the underside of the top portion. In FIG. 4, the objective change controller can also be seen extending from the underside of the top portion.

One or more embodiments of the devices described herein may include a device (e.g., the housing) that optionally further includes one or more selector elements (see, e.g., selector element 65 in FIG. 1). In one or more embodiments, the selector elements may be depressible, may be touch-sensitive, or may be any other suitable type of selector element. The selector elements may be located on (e.g., mounted on, otherwise attached to, etc.) any part of the housing (e.g., a base, an arm, a top portion, a stage, etc.). The selector elements may also take any suitable shape or size. In one or more embodiments, the one or more selector elements may include, but are not limited to, any one or more of the following selector elements: an objective selector element, an image selector element, an advancement selector element, a stain selector element, a display toggle selector element, a marking selector element, and a drawing selector element. In the present disclosure, any of the one or more selector elements may take the form of switches, dials, knobs, etc.

In one or more embodiments, the device (e.g., the housing) may include, in addition to or in place of the objective change controllers previously described herein, one or more objective selector elements. An objective selector element may take any suitable form or shape (e.g., any geometrically or non-geometrically shaped selector element, a depressible selector element, a touch-sensitive selector element, etc.) for manipulation by a user. In one or more embodiments wherein the computer input device is used to, for example, manipulate the display of a digital image, actuation of an objective selector element may be used to communicate a change in the magnification an image on the display apparatus. In one or more preferred embodiments, an objective selector element may be located on any part of the housing. For example, as depicted in the embodiment of FIGS. 2-4, an arm 130 of a housing may include a plurality of objective selector elements, wherein each objective selector element may represent a discrete magnification (e.g., 4×, 10×, 20×, 40×, etc.). An objective selector element may be designed to allow a user to select one of a plurality of discrete magnifications (e.g., 4×, 10×, 20×, 40×) and/or to select a magnification different than the discrete magnifications (e.g., 4.5×, 5×, 6.75×, 7.03×, 13×, 27×, etc.). For example, in some embodiments, the objective selector element may be manipulated to select any magnification from a range of available magnifications based on, for example, the magnifications used when scanning a microscopic tissue section into a digital image (e.g., a histological digital image).

In one or more embodiments, a magnification may be selected by the user depressing, touching, or otherwise actuating the objective selector element. In one or more embodiments, the objective selector elements may be located on the computer input device in a location to allow the objective to be changed with the thumb of the user's hand that is controlling the coarse and/or fine focus controllers, which allows the user's opposite hand to, for example, remain on a reference slide or actuate the x-axis and y-axis stage controllers. In embodiments depicted in FIGS. 2, 3, and 4, objective selector elements can be seen (labeled "4× objective," "10× objective," "20× objective," and "40× objective"), four objective selector elements located on one side of the arm in FIGS. 2 and 3 and four more objective selector elements located on the opposite side of the arm in FIG. 4.

In one or more embodiments, the device (e.g., the housing) may include one or more image selector elements (e.g., a photo selector element, photo button, etc.). An image selector element may take any suitable form or shape (e.g., any geometrically or non-geometrically shaped selector element, a depressible selector element, a touch-sensitive selector element, etc.) for manipulation by a user. In one or more embodiments wherein the computer input device is used to, for example, manipulate the display of a digital image, actuation of an image selector element may be used to create a new digital image that may include all or a portion of a digital image displayed on a display apparatus. In one or more preferred embodiments, an image selector element may be located on any part of the housing (e.g., an arm, a top portion, a stage, a base, etc.). In one or more embodiments, a digital image may be created by the user depressing, touching, or otherwise actuating the image selector element. In one or more embodiments, the image selector element may be pressed by a user without removing the user's hand from a reference slide. In, e.g., the embodiment depicted in FIG. 2, an image selector element 166 can be seen located on the arm 130. In FIG. 4, another image selector element 166 can be seen on the opposite side of the arm 130.

In one or more embodiments, the device (e.g., the housing) may include one or more advancement selector elements. An advancement selector element may take any suitable form or shape (e.g., any geometrically or non-geometrically shaped selector element, a depressible selector element, a touch-sensitive selector element, etc.) for manipulation by a user. In one or more embodiments wherein the computer input device is used to, for example, manipulate the display of a digital image, actuation of an advancement selector element may be used to select a different digital image (e.g., select a different biological case). For example, a series of digital images (e.g., a series of stacked digital images) may be loaded in a queue and actuation of the advancement selector element may be used to select a different digital image (e.g., the next digital image, the previous digital image, etc.) in the queue.

In one or more preferred embodiments, an advancement selector element may be located on any part of the housing (e.g., an arm, a top portion, a stage, a base, etc.). In one or more embodiments, a next or previous digital image in a queue may be selected by the user depressing, touching, or otherwise actuating the advancement selector element. In one or more embodiments, a housing may include advancement selector elements that include a next selector element (e.g., a next button) and a previous selector element (e.g., a previous button), each for selecting a different biological case that may be pre-loaded in a digital queue. In, e.g., the embodiment depicted in FIGS. 2 and 3, two advancement selector elements 167a and 167b can be seen located on the top portion 132. In FIG. 4, another set of two advancement selector elements 167a and 167b can be seen on the opposite side of the top portion 132.

In one or more embodiments, the device (e.g., the housing) may include one or more stain selector elements. A stain selector element may take any suitable form or shape (e.g., any geometrically or non-geometrically shaped selector element, a depressible selector element, a touch-sensitive selector element, etc.) for manipulation by a user. In one or more embodiments wherein the computer input device is used to, for example, manipulate the display of a digital image, actuation of a stain selector element may be used to toggle between stained portions of a digital image. In one or more preferred embodiments, a stain selector element may be located on any part of the housing (e.g., an arm, a top portion, a stage, a base, etc.). In one or more embodiments, the function of the stain selector element may be communicated by the user depressing, touching, or otherwise actuating the stain selector element.

In one or more embodiments, a housing may further include a stain adjustment controller. Actuation of the stain adjustment controller may allow a user to adjust or correct the appearance of all or a portion of a scanned digital image that is over-stained or under-stained. The function of the stain adjustment controller may be incorporated into the stain selector element or may be incorporated into a controller different than the stain selector element. A stain adjustment controller may take any suitable form or shape (e.g., one or more dials, knobs, touch pads, buttons, etc.). In, e.g., the embodiment depicted in FIG. 3, two stain selector elements 168 can be seen located on the top portion 132.

In one or more embodiments, the device (e.g., the housing) may include one or more display toggle selector elements. A display toggle selector element may take any suitable form or shape (e.g., any geometrically or non-geometrically shaped selector element, a depressible selector element, a touch-sensitive selector element, etc.) for manipulation by a user. In one or more embodiments wherein the computer input device is used to, for example, manipulate the display of a digital image, actuation of a display toggle selector element may be used to toggle the screen display on a display apparatus between full screen, split screen, and other screen configurations.

In some embodiments, a display toggle selector element may toggle the display to a configuration that includes a simultaneous display of a plurality of immuno stains of the same case, which may allow comparison of, e.g., immuno expression with the cells of interest on Hematoxylin and Eosin stain (sometimes referred to as "H and E"). H and E is a widely used stain in medical diagnosis and is applied to many histological sections that are evaluated microscopically. Generally, before special cytochemical stains (stains that highlight certain cellular components based on molecular composition) or immunohistochemical stains (stains that highlight cells that express particular proteins) are performed, an H and E stain is evaluated by the pathologists.

One problem that can be difficult for the diagnosing pathologist is comparing the special stain results to the H and E. With a traditional microscope, a pathologist examines the H and E slide and makes a mental note of the location of the cells of interest for that are to be evaluated with additional special stains (e.g., cytochemical and/or immunohistochemical). Often, a pathologist will alternate several times between the H and E section and the special stain(s) to make sure that the appropriate cells are being evaluated. If one were able to see both the H and E (which generally the best stain for highlighting architectural features of a tissue) and one or more special stains (which may highlight cellular features) simultaneously, time could potentially be saved and/or an accurate diagnosis could potentially be facilitated.

In one or more preferred embodiments, a display toggle selector element may be located on any part of the housing (e.g., an arm, a top portion, a stage, a base, etc.). In one or more embodiments, the function of the display toggle selector element may be communicated by the user depressing, touching, or otherwise actuating the display toggle selector element. In, e.g., the embodiment depicted in FIG. 3, two display toggle selector elements 169 can be seen located on the top portion 132.

In one or more embodiments, the device (e.g., the housing) may include one or more marking selector elements. A marking selector element may take any suitable form or shape (e.g., any geometrically or non-geometrically shaped selector element, a depressible selector element, a touch-sensitive selector element, etc.) for manipulation by a user. In one or more embodiments wherein the computer input device is used to, for example, manipulate the display of a digital image, actuation of a marking selector element may be used to mark at least a portion of the digital image for, for example, photographing or further reference.

In one or more preferred embodiments, a marking selector element may be located on any part of the housing (e.g., an arm, a top portion, a stage, a base, etc.). In one or more embodiments, all or a portion of a digital image may be marked by the user depressing, touching, or otherwise actuating the marking selector element. In, e.g., the embodiment depicted in FIG. 3, two marking selector elements 171 can be seen located on the top portion 132.

In one or more embodiments, the device (e.g., the housing) may include one or more drawing selector elements. A drawing selector element may take any suitable form or shape (e.g., any geometrically shaped selector element, a touch sensitive selector element, etc.) for manipulation by the user. In one or more embodiments wherein the computer input device is used to, for example, manipulate the display of a digital image, actuation of a drawing selector element may be used to allow a user to digitally draw on the digital image. As used herein, digitally drawing on the digital image may include, but is not limited to, drawing indicia (e.g., encircling, underlining, or adding any other suitable indicia, etc.) that may identify regions of interest in the digital image and/or drawing a perimeter around a region for further analysis based on, for example, computer assisted diagnostic (CAD) algorithms. In one or more preferred embodiments, a drawing selector element may be located on any part of the housing (e.g., an arm, a top portion, a stage, a base, etc.).

In one or more embodiments, the function of the drawing selector element may be communicated by the user depressing, touching, or otherwise actuating the drawing selector element. In, e.g., the embodiment depicted in FIGS. 2-4, two drawing selector elements 172 can be seen located on the top portion 132.

In some embodiments, the device (e.g., the housing) may further include a pointer controller. A pointer controller may take any suitable form or shape (e.g., a touchpad, a mouse-like device, a joystick, a rollerball, etc.) for manipulation by the user. In one or more embodiments wherein the computer input device is used to, for example, manipulate the display of a digital image, actuation of the pointer controller may be used to allow a user to manipulate a pointer or cursor on the display apparatus (e.g., translationally move a cursor across a screen of a display apparatus). For example, after the drawing selector element is actuated, movement of the pointer controller may effect digital drawing on the digital image. The pointer controller may also allow the user the functionality of pointing to a region of interest on a digital image, similar to the functionality of, for example, a mouse or rollerball. The pointer controller may also be complimented with one or more pointer selector elements for, for example, clicking-and-dragging functions or selecting various functions from one or more menus available in image display software or an operating system.

In one or more preferred embodiments, a pointer controller may be located on any part of the housing (e.g., an arm, a top portion, a stage, a base, etc.). In one or more embodiments, the function of the pointer controller may be communicated by the user moving, rolling, or otherwise actuating the pointer controller. In the embodiment depicted in FIGS. 2-4, a pointer controller 163 can be seen extending from the top portion 132. The depicted pointer controller 163 is din the form of a stick connected to a rollerball-type controller in the top portion 132.

In one or more embodiments, the device (e.g., the top portion) may optionally include a contrast controller. The contrast controller may take any suitable form or shape (e.g., a cylindrical dial, a knob, one or more buttons, etc.) for manipulation by a user. The contrast controller may be located on any portion of the housing (e.g., an arm, a base, a stage, a top portion, etc.). In one or more embodiments wherein the computer input device is used to, for example, manipulate the display of a digital image, actuation of the contrast controller may be used to adjust the contrast of a digital image on a display apparatus. Adjusting the contrast of the digital image may include, but is not limited to, adjustments to the digital image and adjusting the contrast settings of a display apparatus.

Even further, in one or more embodiments, the device (e.g., the housing) of a computer input device of the present disclosure may optionally include one or more other functional selector elements or controllers. For example, the housing of a computer input device may include controls for settings for a display apparatus and/or to adjust one or more features and/or characteristics of the digital image, e.g. an H or E component of the digital image, contrast, brightness, color balance, etc.

The computer input device of the present disclosure may also include additional optional functional selector elements or controllers to control functionality that is not currently available or recognized. In an embodiment depicted in FIG. 2, three optional functional selector elements or controllers can be seen extending from the base 120.

In one or more embodiments of the present disclosure, the computer input device may be configured to be familiar to the user and/or ergonomic. For example, a computer input device may be used in, for example, pathology, to make various diagnoses of microscopic tissue sections. A computer input device may be configured to be familiar, for example, when the shape of the computer input device generally resembles a traditional light microscope. In one or more embodiments, the computer input device may include some or all of the same dimensions and mechanical feel as a light microscope. Although the computer input device may resemble a light microscope, in some embodiments, the computer input device optionally may not include a working eyepiece into which one can look to see an image, optionally may not include any optical lenses associated with an eyepiece, and optionally may not include a working camera. Further, the controls described herein may be located on the computer input device in locations that may be intuitive to a user. FIGS. 2, 3, and 4 depict at least one embodiment in which the computer input device generally resembles a light or optical microscope.

The computer input device may also be ergonomically designed. For example, in some embodiments, the distance between the bottom portion of the base of the housing and the coarse focus controller may be adjustable. Likewise, the distance between the bottom portion of the base of the housing and the fine focus controller may be adjustable. In the computer input device of the present disclosure, the coarse and fine focus controllers do not have any mechanical connection with any optics in the computer input device, such as would be the case in a light microscope, so the coarse and fine focus controllers may be located at any suitable height or location on the computer input device. For example, in some embodiments of the present disclosure, a user may adjust the coarse or fine focus controllers to a position that is ergonomic or comfortable for the user (e.g., low enough to rest the user's hand on a supporting surface, etc.).

In addition, a computer input device of the present disclosure may be configured for use by both a left-handed user and a right-handed user. For example, in some embodiments, one or more of the controllers or selector elements may be duplicated wherein a first particular controller may be configured for manipulation by a left hand of a user and a second particular controller configured for manipulation by a right hand of a user and designed to perform the same function of the first particular controller. For example, the stage of the housing may include a second x-axis stage controller and a second y-axis stage controller. The second x-axis stage controller may extend from the stage and may be rotatable about a seventh axis, wherein the seventh axis may be generally aligned with the z-axis. Likewise, the second y-axis stage controller may extend from the stage and may be rotatable about an eighth axis, wherein the eighth axis may be generally aligned with the z-axis. In some embodiments, the seventh and eighth axes may be the same axis.

As another example of the device (e.g., the housing) including duplicate controllers for the left hand and right hand of a user, an arm may include a second coarse focus controller that may extend from the arm and may be rotatable about the fourth axis; and/or a second fine focus controller that may extend from the arm and may be rotatable about the fifth axis.

In one or more embodiments, the device (e.g., the housing) may also include two or more selector elements located on (e.g., mounted to, etc.) the housing, wherein the two or more selector elements may include, but are not limited to, two objective selector elements, two image selector elements, two advancement selector elements, two stain selector elements, two display toggle selector elements, two marking selector elements, and/or two drawing selector elements. In such embodiments, selector elements may be arranged, wherein the two selector elements for a particular function are located such that one may be for both right-handed use and one may be for left-handed use.

In one or more embodiments, a computer input device as described herein may also include a slide 90 (e.g., a reference slide) (as depicted in connection with FIG. 1). In some embodiments, the computer input device may be configured to detect movement of a reference slide on the stage (e.g., on the top surface, on the slide sensor pad, in the xy-plane, etc.) and translate such movement to manipulation of a digital image on a display apparatus (e.g., movement of the digital image on a digital image display operably connected to the computer input device). In one or more embodiments, the slide sensor pad on the stage may include an optical sensor, which may be capable of detecting movement of the reference slide within the xy-plane (i.e., translational movement in any direction across the stage). In some embodiments, the slide sensor pad may include an optical sensor. For example, an optical sensor used in the slide sensor pad may be similar to those employed in an optical computer mouse.

Translational movement of a reference slide 90 on the stage and corresponding translation to translational movement of the digital image on the display apparatus may, for example, simulate the movement of a microscope slide on a light microscope stage corresponding to the movement of a microscope sample within a field of view in a light microscope. In some embodiments, by correlating movement of a reference slide on the stage of the computer input device, the computer input device allows a user to move to different regions of the digital image by moving the reference slide. For example, at high magnifications, a user may easily and quickly move the reference slide a short distance which could translate to movement through one or more screens worth (e.g., more than 10, more than 100, more than one thousand screens worth) of the digital image.

In some embodiments, the reference slide 90 may be constructed of glass or any other suitable material or materials (e.g., polymer, wood, ceramic, fabric, natural, synthetic, etc.). For example, a reference slide may be a glass slide. In some embodiments, the reference slide may include a pattern (e.g., a pattern imprinted, embedded, or otherwise included on one or more major surfaces, the pattern detectable by the slide sensor pad). The reference slide may include a pattern on one or more surfaces of the reference slide and/or may include a pattern detectable from one or more directions from the reference slide. In one or more embodiments, the movement of the reference slide may be detected by any suitable detector which may be included in the slide sensor pad, stage, or any other suitable location on the computer input device.

In one or more embodiments, a plurality of controllers may be simultaneously actuated, wherein simultaneous actuation of a plurality of controllers effects simultaneous manipulation of a digital image on a display apparatus. In some embodiments, focus controllers (e.g., coarse and/or fine focus controllers) may be actuated simultaneously with actuating an objective selector element and/or an objective change controller, thereby effecting simultaneous adjustments in focus and magnification. In one or more embodiments, the reference slide may be translationally manipulated (or the slide sensor pad may be otherwise manipulated) simultaneously with actuating the focus controllers and actuating an objective controller and/or an objective change controller, thereby effecting changes in focus, magnification, and field of view on the display apparatus. As used herein, "simultaneous actuation" means that at least two controls are actuated (e.g., adjusted, used, pressed, rotated, etc.) at the same time and thereby the computer input device effects changes to the display of the digital image on the display apparatus that appear to be seamless to the naked human eye. In one or more embodiments, the computer input device is capable of transmitting one or more signals to communicate one or more types of digital image manipulation, wherein the one or more manipulations may appear on the display of the display apparatus to be seamless. Sufficient capacity of a central processing unit and associated video cards and computer memory may allow for these simultaneous actuations to appear seamlessly on a display apparatus.

The computer input device of the present disclosure may be operatively connected to a central processing unit (CPU) having software (e.g., image display software) loaded therein. The computer input device may transmit (e.g., send, communicate, etc.) one or more signals to the central processing unit and may, for example, interact with image display software. The computer input device may be configured such that each of the controllers and selector elements correspond with a feature or function of image display software. In some embodiments, the computer input device may control, manipulate, or modify a digital image (e.g., a scanned digital image of a slide, etc.) displayed on a display apparatus (e.g., a computer screen, etc.). In one or more embodiments, when used in conjunction with high resolution scanned slide digital images and image software, the computer input device of the present disclosure may allow a pathologist to manipulate a digital image with improved facility and efficiency as if the pathologist had a traditional light microscope.

For example, the computer input device of the present disclosure may allow a user to move through (e.g., view all or a portion of, etc.) a slide image at any magnification and focus through multiple planes of the image, when employing a digital image stacking feature, with improved efficiency as if using a traditional light microscope. In some embodiments, this improved efficiency may arise from the computer input device of the present disclosure including the same or analogous controls as a traditional light microscope.

As used herein a "digital image" includes one or more digital images (e.g., one or more scanned digital images of, for example, biological material) or a virtual stack of digital images, wherein each digital image in a stack represents a scan of a microscopic tissue section at a particular focus and depth (e.g., a plane) within the sample.

In one or more embodiments of the present disclosure, the computer input device may transmit signals to, for example, a central processing unit through a wire and/or wirelessly. For example, the computer input device may be operatively connected to a central processing unit via a wire plugged into an input port (e.g., a parallel port, USB port, serial port, firewire port, etc.) of the CPU. In one or more embodiments, the computer input device may transmit signals wirelessly to the central processing unit, via a wireless network. Further, the computer input device of the present disclosure may be locally connected with a central processing unit, which is connected to an electronic network (e.g., a network of computers), such that the computer input device may manipulate a digital image saved on a different central processing unit or server in the electronic network.

The following provides further description of one or more embodiments of the present disclosure:

The computer input device of the present disclosure and use of the same may improve various aspects of analyzing tissue specimens in, for example, pathology education and/or autopsy procedures. Tissue specimens could be sent to specialized histology laboratories that could prepare slides, scan the slides, and send the images to pathologists across long distances (perhaps around the world). Scanned images may be more quickly transmitted through electronic networks in comparison to waiting for the arrival of an actual slide by traditional delivery methods and for secretarial processing after arrival. Images and diagnoses may more easily and quickly be shared with consultants, resulting in more timely diagnoses and improved patient care. For example, a pathologist may order and quickly receive the image of any requested special stains that would be diagnostically useful but otherwise difficult or impossible to obtain, and would be able to receive reimbursement for the interpretation of the special stain that the pathologist would have had to send out. Further, cases may be pre-loaded in a digital queue, which may result in more cases to be analyzed per unit of time, perhaps resulting in increased revenue for the user. The identity of the sample may be loaded into the digital image, perhaps reducing transcription and/or diagnostic errors. Further, the computer input device of the present disclosure may provide improved ergonomics for the user, since the user would not need to be hunched over while peering into a light microscope.

Analysis of digital images using the computer input device of the present disclosure may allow the user to perform one or more digital analyses of the specimen, including, but not limited to, calculation of the percent tumor of a specimen (prognostic/diagnostic significance); calculation of tumor size and invasion depth, which can be important for several types of cancer for diagnosis, prognosis, and patient management; tracking the region that has been evaluated; digitally marking regions or cells of interest; and diagnostic regions of the case can be easily highlighted and included in a report.

All references and publications cited herein are expressly incorporated herein by reference in their entirety into this disclosure. Illustrative embodiments of this disclosure are discussed and reference has been made to possible variations within the scope of the claims. These and other variations and modifications in the disclosure will be apparent to those skilled in the art without departing from the scope of the claims, and it should be understood that this disclosure is not limited to the illustrative embodiments set forth herein. Accordingly, the disclosure is to be limited only by the claims provided below and equivalents thereof.

What is claimed is:

1. A computer input device for manipulating a digital image displayed on a display apparatus operably connected to the computer input device, the device comprising:
a housing comprising a base having a bottom portion for optionally resting on a support surface, an arm extending upward from the base and terminating at a top portion, and a stage extending outward from the arm at a location intermediate the base and the top portion;
wherein the stage comprises a distal portion proximate the arm, a proximal portion opposite the distal portion, wherein a y-axis passes through the distal portion, the proximal portion, and the arm, wherein the stage further comprises a top surface defining an xy-plane, wherein the xy-plane optionally generally aligns with the bottom portion of the base, wherein the xy-plane comprises the y-axis and an x-axis transverse to the y-axis;
an x-axis stage controller attached to the housing and configured to communicate lateral movement of the digital image displayed on the display apparatus along an x-axis, the x-axis stage controller optionally extending from the stage and optionally rotatable about a first axis that may be generally aligned with the z-axis, wherein the z-axis is generally transverse to the xy-plane; and
a y-axis stage controller attached to the housing and configured to communicate lateral movement of the digital image displayed on the display apparatus along a y-axis, the y-axis stage controller optionally extending from the stage and optionally rotatable about a second axis that may be generally aligned with the z-axis, wherein the first and second axes are, optionally, the same axis.

2. The computer input device of claim 1, wherein the device further comprises a brightness controller configured to change brightness of the digital image displayed on the display apparatus; wherein the brightness controller optionally extends from the base toward the stage and optionally rotates about a third axis optionally generally aligned with the z-axis.

3. The computer input device of claim 1, wherein the device further comprises a coarse focus controller configured to change focus of the digital image displayed on the display apparatus, wherein the coarse focus controller optionally extends from the arm and optionally rotates about a fourth axis optionally generally aligned with the x-axis.

4. The computer input device of claim 1, wherein the device further comprises a fine focus controller configured to change focus of the digital image displayed on the display apparatus, wherein the fine focus controller optionally extends from the arm and optionally rotates about a fifth axis optionally generally aligned with the x-axis, wherein the fourth and fifth axes are optionally the same axis.

5. The computer input device of claim 1, wherein the device further comprises an objective change controller configured to change magnification of the digital image displayed on the display apparatus, wherein the objective change controller optionally extends from the base toward the stage and optionally rotates about a sixth axis optionally generally aligned with the z-axis.

6. The computer input device of claim 5, wherein objective change controller is configured to select one of a plurality of discrete magnifications when changing the magnification of the digital image displayed on the display apparatus.

7. The computer input device of claim 1, wherein the device further comprises an objective selector element attached to the housing and configured to change magnification of the digital image displayed on the display apparatus.

8. The computer input device of claim 1, wherein the device further comprises an image selector element attached to the housing and configured to create a new digital image including all or a portion of the digital image displayed on the display apparatus.

9. The computer input device of claim 1, wherein the device further comprises an advancement selector element attached to the housing and configured to selected a different digital image for display on the display apparatus.

10. The computer input device of claim 8, wherein the advancement selector element comprises a next selector element for selecting digital images pre-loaded in a digital queue.

11. The computer input device of claim 1, wherein the device further comprises a stain selector element attached to the housing and configured to toggle between stained portions of the digital image displayed on the display apparatus.

12. The computer input device of claim 1, wherein the device further comprises a stain adjustment controller attached to the housing and configured to adjust the stained appearance of all or a portion of the digital image displayed on the display apparatus.

13. The computer input device of claim 1, wherein the device further comprises a display toggle selector element attached to the housing and configured to toggle a display on the display apparatus between a full screen, split screen, and other screen configurations.

14. The computer input device of claim 1, wherein the device further comprises a marking selector element attached to the housing and configured to mark at least a portion of the digital image displayed on the display apparatus.

15. The computer input device of claim 1, wherein the device further comprises a drawing selector element attached to the housing and configured to digitally draw on the digital image displayed on the display apparatus.

16. The computer input device of claim 15, wherein the drawing selector element is configured to draw indicia on the digital image.

17. The computer input device of claim 1, wherein the device further comprises a pointer controller attached to the housing and configured to manipulate a pointer or cursor on the digital image displayed on the display apparatus, wherein the pointer controller is optionally a joystick controller or a roller ball controller.

18. The computer input device of claim 1, wherein the device comprises a slide sensor pad on the top surface of the stage, the slide sensor pad comprising one or more sensors configured to detect movement on the slide sensor pad within the xy-plane.

19. The computer input device of claim 18, wherein the device comprises a reference slide and wherein the one or more sensors are configured to detect movement of the reference slide on the slide sensor pad.

20. The computer input device of claim 19, wherein the reference slide comprises a design on one or more sides of the reference slide.

21. The computer input device of claim 19, wherein movement of the reference slide on the slide sensor pad translates to movement of the digital image displayed on the display apparatus.

* * * * *

UNITED STATES PATENT AND TRADEMARK OFFICE
CERTIFICATE OF CORRECTION

PATENT NO. : 8,896,620 B2  
APPLICATION NO. : 13/254401  
DATED : November 25, 2014  
INVENTOR(S) : Jared M. Orrock

Page 1 of 1

It is certified that error appears in the above-identified patent and that said Letters Patent is hereby corrected as shown below:

In the Claims

In column 18, claim 4, line 35, "claim 1" should be "claim 3".

Signed and Sealed this  
Eighth Day of March, 2016

Michelle K. Lee  
*Director of the United States Patent and Trademark Office*